United States Patent
Capetan et al.

Patent Number: 5,885,243
Date of Patent: *Mar. 23, 1999

[54] LIQUEFACTION HANDPIECE

[75] Inventors: Thomas G. Capetan, Corona Del Mar; Donald M. Cohen, Irvine, both of Calif.

[73] Assignee: Alcon Laboratories, Inc., Fort Worth, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 766,538

[22] Filed: Dec. 11, 1996

[51] Int. Cl.$^6$ .................................................. A61M 1/00
[52] U.S. Cl. ............................................................ 604/27
[58] Field of Search .......................... 604/19–22, 27–37, 604/43, 113, 51, 114, 54, 118, 248; 606/107, 159, 24, 25, 169–171; 623/4–6; 607/96, 99

[56] References Cited

U.S. PATENT DOCUMENTS

| | | |
|---|---|---|
| 3,589,363 | 6/1971 | Banke et al. . |
| 4,078,564 | 3/1978 | Spina et al. ............................. 128/216 |
| 4,223,676 | 9/1980 | Wuchinich et al. . |
| 4,246,902 | 1/1981 | Martinez . |
| 4,493,694 | 1/1985 | Wuchinich . |
| 4,515,583 | 5/1985 | Sorich . |
| 4,589,415 | 5/1986 | Haaga . |
| 4,609,368 | 9/1986 | Dotson, Jr. . |
| 4,744,360 | 5/1988 | Bath ........................................... 604/20 |
| 4,869,715 | 9/1989 | Sherburne . |
| 4,922,902 | 5/1990 | Wuchinich et al. . |
| 4,989,583 | 2/1991 | Hood . |
| 5,154,694 | 10/1992 | Kelman . |
| 5,191,883 | 3/1993 | Lennox et al. . |
| 5,207,674 | 5/1993 | Hamilton ................................. 606/20 |
| 5,261,883 | 11/1993 | Hood et al. . |
| 5,445,636 | 8/1995 | Bretton . |
| 5,445,637 | 8/1995 | Bretton . |
| 5,616,120 | 4/1997 | Andrew et al. ........................... 604/28 |
| 5,733,263 | 3/1998 | Wheatman .............................. 604/141 |

FOREIGN PATENT DOCUMENTS

WO 96/24314  8/1996  WIPO .

*Primary Examiner*—John D. Yasko
*Assistant Examiner*—Manuel Mendez
*Attorney, Agent, or Firm*—Jeffrey S. Schira

[57] ABSTRACT

A surgical handpiece having at least two lumens mounted to a body. One lumen is used for aspiration, the second lumen is used to inject heated surgical fluid for liquefying a cataractous lens. A portion of the second lumen is surrounded by an insulated heating element that heats the surgical fluid as it passes through the second lumen. The handpiece may also contain a device for delivering the surgical fluid through the second lumen in metered pulses of a defined volume.

18 Claims, 5 Drawing Sheets

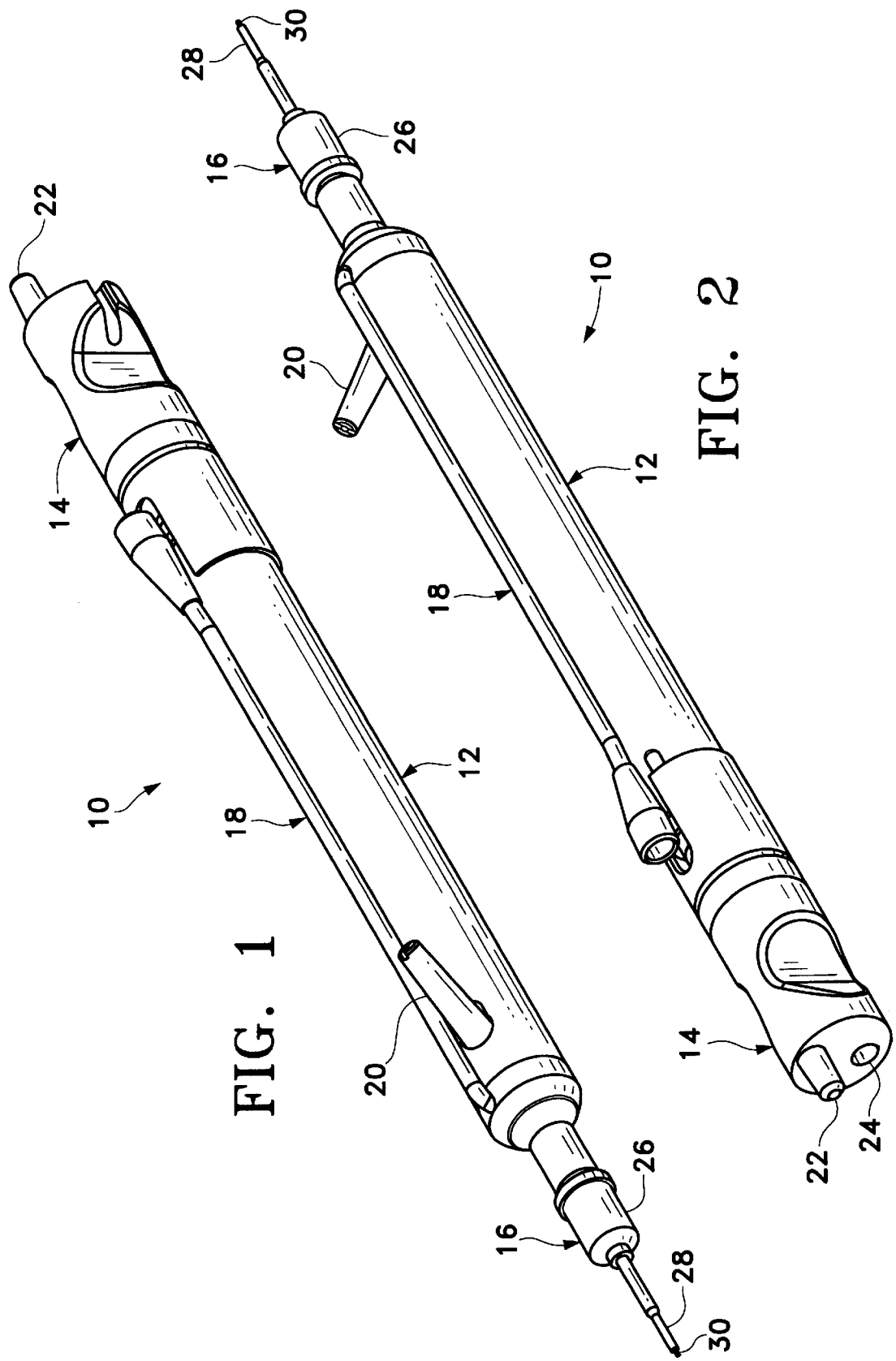

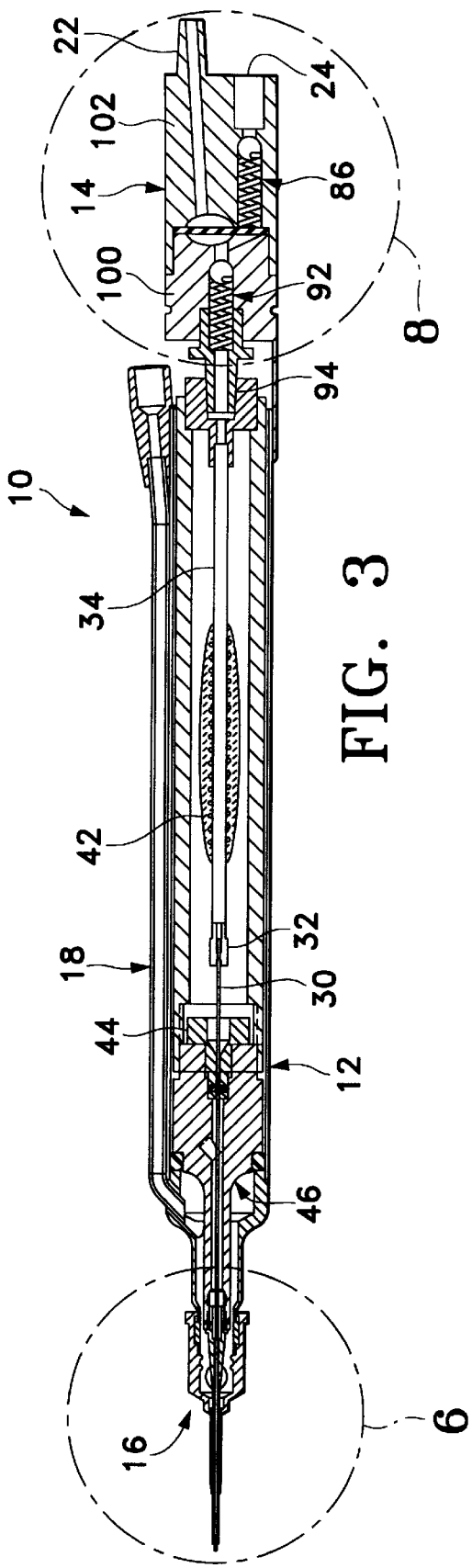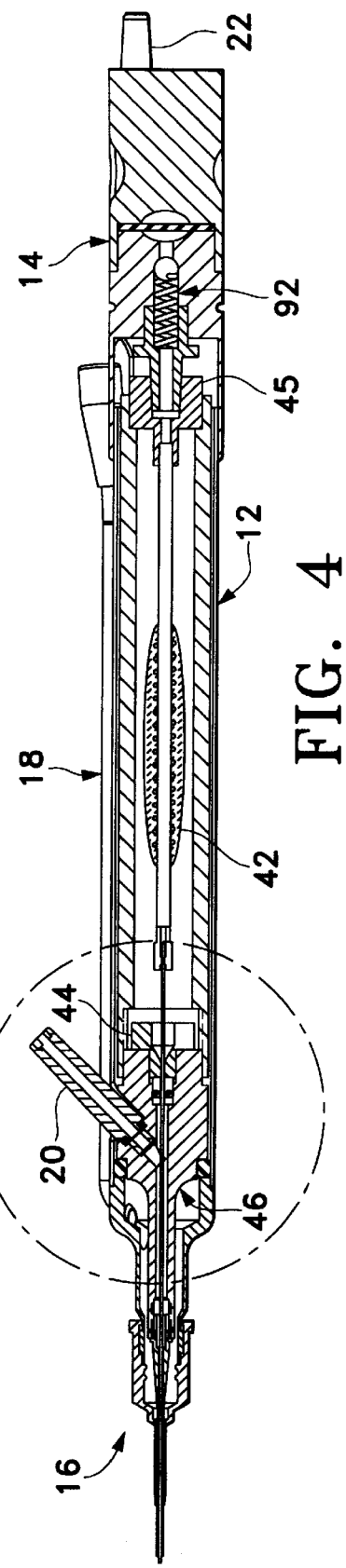

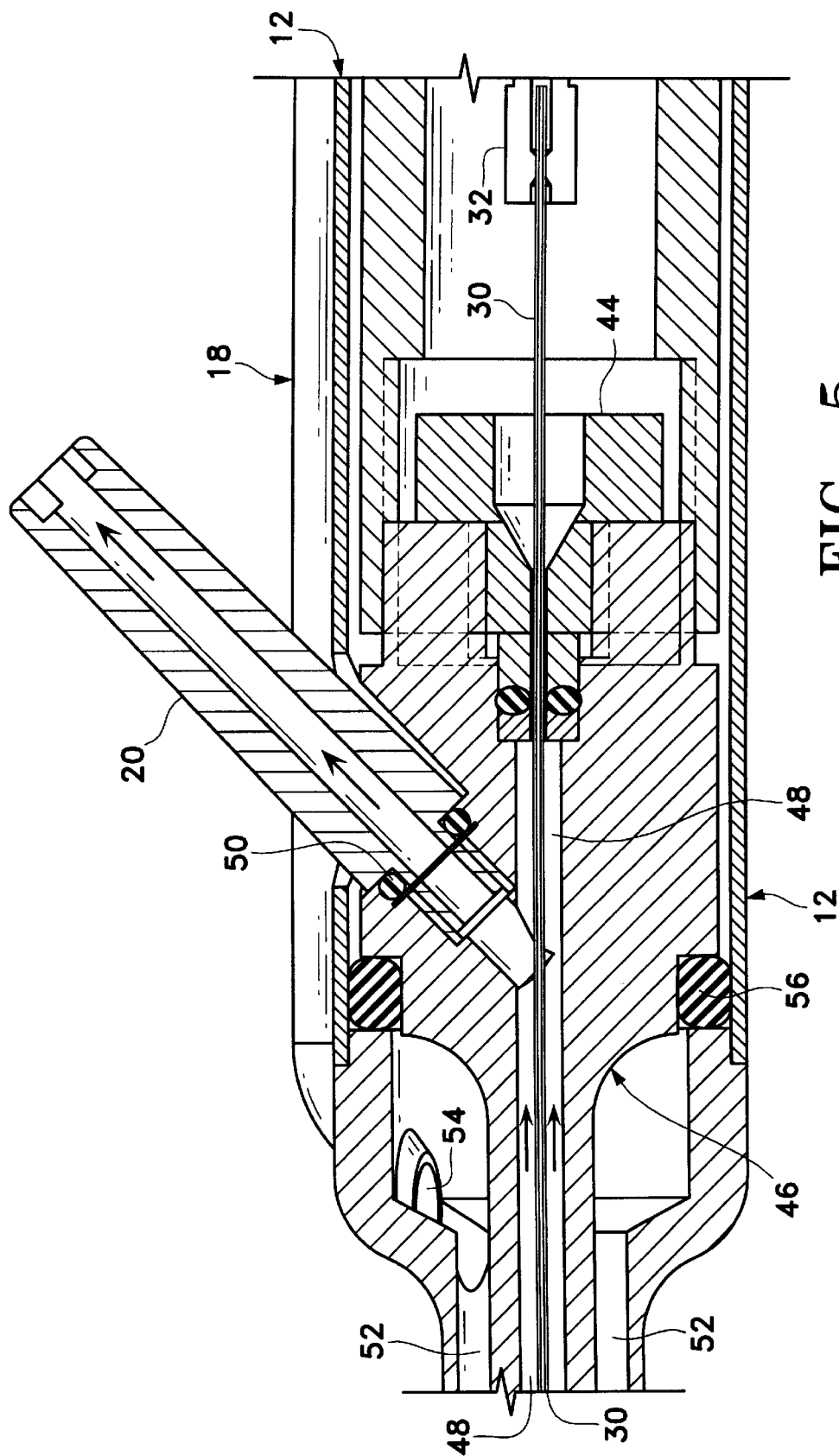

LIQUEFACTION HANDPIECE

BACKGROUND OF THE INVENTION

This invention relates generally to the field of cataract surgery and more particularly to a handpiece for practicing the liquefaction technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution, as is the injection of a relatively cool solution, thereby quickly cooling and removing the heated solution. This technique is more fully described in U.S. patent application Ser. No. 08/384,655 (PCT Application No. PCT/US95/17072), which is published as WIPO Publication No. WO 96/24314, the entire contents of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

Therefore, a need continues to exist for a surgical handpiece that can heat internally the solution used to perform the liquefaction technique.

BRIEF SUMMARY OF THE INVENTION

The present invention improves upon the prior art by providing a surgical handpiece having at least two lumens mounted to a body. At least one lumen is used for aspiration and at least one other lumen is used to inject heated surgical fluid for liquefying a cataractous lens. A portion of the second lumen is surrounded by an insulated heating element that heats the surgical fluid as it passes through the second lumen. The handpiece may also contain other lumens for injecting relatively cool surgical fluid and a device for delivering the surgical fluid through these other lumen(s) in metered pulses of variable volume and/or pressure.

Accordingly, one objective of the present invention is to provide a surgical handpiece having at least two lumens.

Another objective of the present invention is to provide a surgical handpiece having a heating element.

Another objective of the present invention is to provide a surgical handpiece having a device for delivering the surgical fluid through the handpiece in metered pulses.

These and other advantages and objectives of the present invention will become apparent from the detailed description and claims that follow.

BRIEF DESCRIPTION OF THE DRAWINGS

FIG. 1 is a front, upper left perspective view of the handpiece of the present invention.

FIG. 2 is a rear, upper right perspective view of the handpiece of the present invention.

FIG. 3 is a cross-sectional view of the handpiece of the present invention taken along a plane passing through the irrigation channel.

FIG. 4 is a cross-sectional view of the handpiece of the present invention taken along a plane passing through the aspiration channel.

FIG. 5 is an enlarged partial cross-sectional view of the handpiece of the present invention taken at circle 5 in FIG. 4.

DETAILED DESCRIPTION OF THE INVENTION

Figure 6:
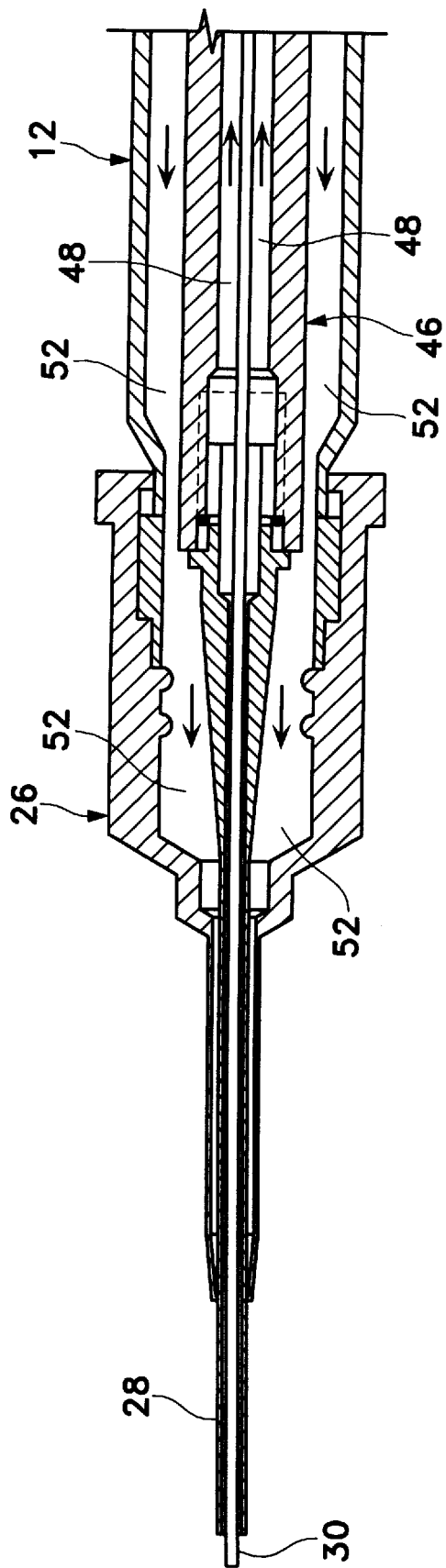
FIG. 6 is an enlarged partial cross-sectional view of the handpiece of the present invention taken at circle 6 in FIG. 3.

Handpiece 10 of the present invention generally includes handpiece body 12, injection device 14 and operative tip 16. Body 12 generally includes external irrigation lumen 18 and aspiration fitting 20. Body 12 is similar in construction to well-known in the art phacoemulsification handpieces and may be made from titanium or stainless steel. Injection device 14 includes pressure port 22 and surgical fluid port 24. Suitable injection devices 14 are commercially available from Alcon Laboratories, Inc., Fort Worth, Tex. and operate in the manner described below. As best seen in FIG. 6, operative tip 16 includes tip/cap sleeve 26, needle 28 and lumen 30. Sleeve 26 may be any suitable commercially available phacoemulsification tip/cap sleeve. Needle 28 may be any commercially available hollow phacoemulsification cutting tip, such as the TURBOSONICS tip available from Alcon Laboratories, Inc., Fort Worth, Tex. Lumen 30 may be any suitably sized tubing to fit within needle 28, for example 29 gauge hypodermic needle tubing.

Figure 7:
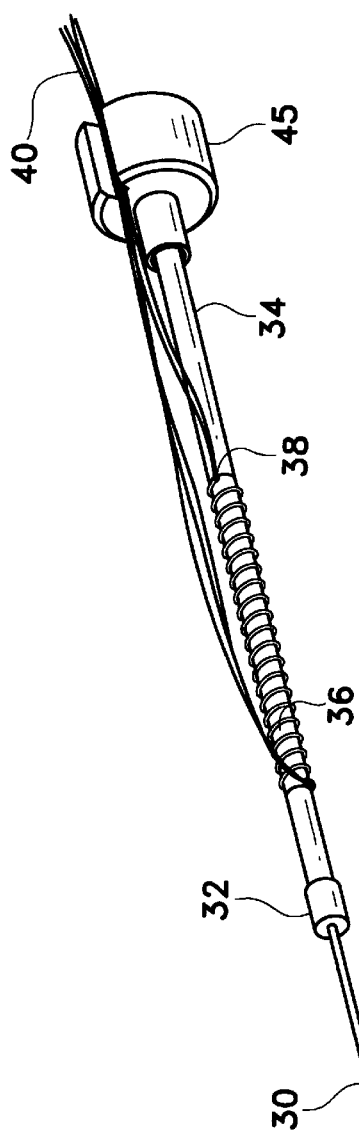
FIG. 7 is a perspective view of the internal heated lumen of the present invention.

As best seen in FIG. 7, lumen 30 is free on the distal end and connected by means of fitting 32 to heater cartridge 34 on the proximal end. Lumen 30, fitting 32 and cartridge 34 may be sealed fluid tight by any suitable means having a relatively high melting point, such as silver solder. Cartridge 34 may be made from thin wall hypodermic tubing (for example, 0.082 inches outside diameter and 0.078 inches inside diameter) or any other suitable material. Surrounding cartridge 34 is insulating sleeve 36, which may be made of any suitable material, such as polyimide, which is an electrical insulator and which resists damage at high temperatures. Attached to sleeve 36 is heater 38 which is preferably a resistive wire, such as a nichrome wire (80% nickel, 20% chrome), although other heating devices may also be used. While any suitably sized wire may be used, approximately 100 turns of a 0.010 inch diameter wire has been found to give satisfactory results. Heater 38 is connected to external power source (not shown) through cables 40, which may be 22 gauge, insulated, stranded, copper wire. Heater 38 and sleeve 36 are surrounded by ceramic insulator 42, which may be a ceramic cement or any other suitable material preferably having a degration temperature in excess of 500° C. Lumen 30 and cartridge 34 are held within body 12 by sealing spacers 44 and 45.

As best seen in FIG. 5, fitting 44 holds lumen 30 within bore 48 of aspiration horn 46. Bore 48 communicates with fitting 20, which is journaled into horn 46 and sealed with O-ring seal 50 to form an aspiration pathway through horn 46 and out fitting 20. Horn 46 is held within body 12 by O-ring seal 56 to form irrigation lumen 52 which communicates with irrigation lumen 18 at port 54.

Figure 8:
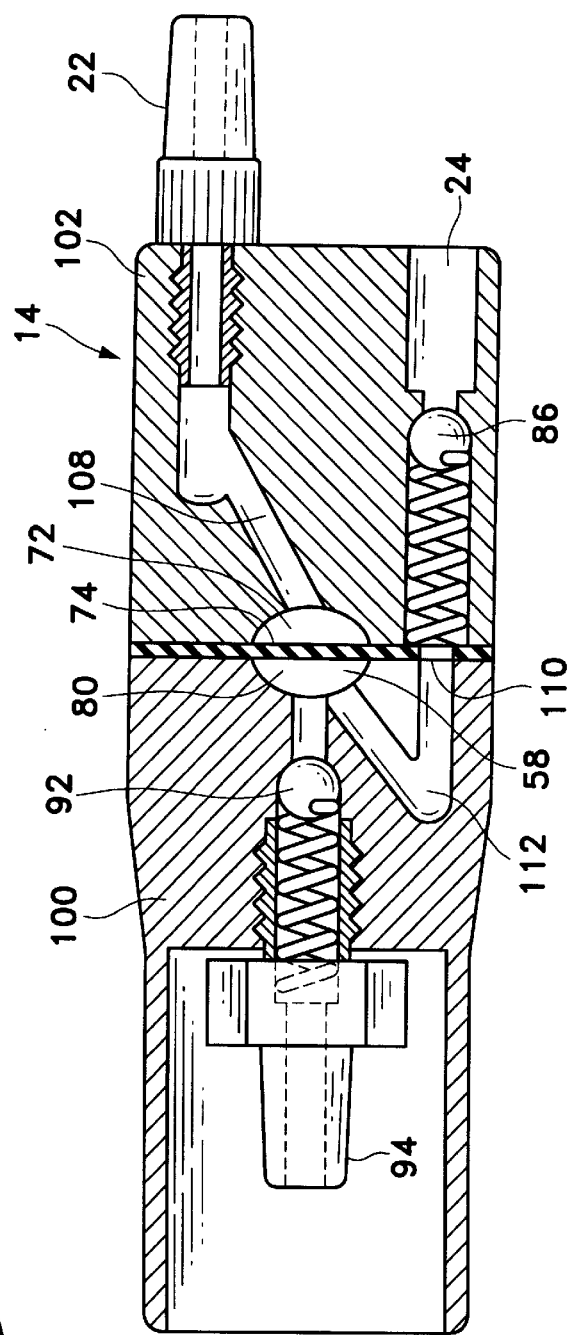
FIG. 8 is an enlarged partial cross-sectional view of the handpiece of the present invention taken at circle 8 in FIG. 3.

As best seen in FIG. 8, injection device 14 is assembled from a first housing 100 and a second housing 102 separated by a flexible diaphragm 74. Housing 100 contains a concave cavity 80 that corresponds to concave cavity 72 in housing 102 that together form pumping chamber 58. In use, suction is applied to port 22 and is communicated to cavity 72 through passage 108, causing diaphragm to be pulled toward cavity 72. Movement of diaphragm 74 toward cavity 72 causes a vacuum to be formed in cavity 80. Vacuum in cavity 80 draws open check valve 86 allowing surgical fluid to enter cavity 80 through port 24, passage 112 and passage 110 in diaphragm 74. Once cavity 80 is filled with irrigation fluid, pressure is applied to port 22, causing diaphragm 74 to be pushed toward cavity 80 and away from cavity 72. This movement causes the irrigation fluid in cavity 80 to be expelled out through check valve 92 and port 94 and into cartridge 34 through fitting 45. A more complete description of the operation of injection device 14 is given in U.S. Pat. No. 5,261,883, the entire contents of which is incorporated herein by reference.

In use, irrigation lumen 18 is connected to a source of surgical fluid (e.g., saline solution) that is cooled or at ambient temperature. Port 20 is connected to a source of vacuum. Port 22 is connected to the pressure drive for injection device 14. Port 24 is connected to a source of surgical fluid (e.g., saline solution) which may be warmed or at ambient temperature. Cable 40 is connected to a suitable source of power. Surgical fluid is injected out of port 94 in injection device 14 and into cartridge 34, where it is heated to the appropriate temperature (approximately 45° C. to 105° C.) by heater 38. The heated fluid then passes through fitting 32, into lumen 30 and out of lumen 30 at the operative site. Simultaneously or independently with the injection of the heated fluid, aspiration may be applied through port 20, bore 48 and the hollow bore of needle 28 so that the heated fluid is aspirated away from the operative site. Cooled or ambient surgical fluid is delivered to the operative site through lumen 18, port 54 and lumen 52 to provide a quenching fluid, to maintain constant pressure within the operative site and to provide an irrigation vehicle for removal of the liquefied lens.

This description is given for purposes of illustration and explanation. It will be apparent to those skilled in the relevant art that changes and modifications may be made to the invention described above without departing from its scope or spirit.

We claim:

1. A liquefaction handpiece, comprising:
   a) a body;
   b) a first irrigation lumen mounted internal to the body; and
   c) a heater cartridge forming a portion of the first irrigation lumen the heater cartridge mounted internal to the body and made from thin wall hyperdermic tubing surrounded by an electrical insulating sleeve and a resistive heater, the heater being surrounded by an insulator and being capable of heating a surgical fluid within the first irrigation lumen to a temperature of approximately 45° C. to 105° C.

2. The handpiece of claim 1 further comprising an injection device in communication with the first irrigation lumen for injecting the surgical fluid into the first irrigation lumen.

3. The handpiece of claim 1 further comprising a second irrigation lumen.

4. The handpiece of claim 2 wherein the second irrigation lumen is mounted external to the body.

5. The handpiece of claim 1 wherein the heater is a resistive wire.

6. A liquefaction handpiece, comprising:
   a) a body;
   b) a first irrigation lumen and an aspiration lumen mounted internal to the body;

c) a second irrigation lumen mounted external to the body; and d) a heater cartridge forming a portion of the first irrigation lumen, the heater cartridge being made from thin wall hyperdermic tubing surrounded by an electrical insulating sleeve and a resistive heater, the heater surrounded by an insulator.

7. The handpiece of claim 6 further comprising an injection device in communication with the first irrigation lumen for injecting a surgical fluid into the first irrigation lumen.

8. The handpiece of claim 6 wherein the heater is capable of heating a surgical fluid within the first irrigation lumen to a temperature of approximately 45° C. to 105° C.

9. The handpiece of claim 6 wherein the heater is a resistive wire.

10. A liquefaction handpiece, comprising:

a) a body having a hollow interior;

b) a first irrigation lumen and an aspiration lumen mounted within the hollow interior; and c) a heater cartridge forming a portion of the first irrigation lumen, the heater cartridge being made from thin wall hyperdermic tubing surrounded by an electrical insulating sleeve and a resistive heater, the heater surrounded by an insulator.

11. The handpiece of claim 10 wherein the heater is capable of heating a surgical fluid within the first irrigation lumen to a temperature of approximately 45° C. to 105° C.

12. The handpiece of claim 10 wherein the heater is a resistive wire.

13. The handpiece of claim 10 further comprising an injection device in communication with the first irrigation lumen for injecting a surgical fluid into the first irrigation lumen.

14. The handpiece of claim 10 further comprising a second irrigation lumen.

15. The handpiece of claim 14 wherein the second irrigation lumen is mounted external to the body.

16. A liquefaction handpiece, comprising:

a) a body having a hollow interior;

b) a first irrigation lumen and an aspiration lumen mounted within the hollow body;

c) a second irrigation lumen mounted external to the body;

d) an injection device in communication with the first irrigation lumen for injecting a surgical fluid into the first irrigation lumen; and e) a heater cartridge forming a portion of the first irrigation lumen, the heater cartridge being made from thin wall hyperdermic tubing surrounded by an electrical insulating sleeve and a resistive heater, the heater surrounded by an insulator.

17. The handpiece of claim 16 wherein the heater is capable of heating the surgical fluid within the first irrigation lumen to a temperature of approximately 45° C. to 105° C.

18. The handpiece of claim 16 wherein the heater is a resistive wire.

* * * * *

UNITED STATES PATENT AND TRADEMARK OFFICE
CERTIFICATE OF CORRECTION

PATENT NO. : 5,885,243
DATED : March 23, 1999
INVENTOR(S) : Capetan, et al

It is certified that error appears in the above-identified patent and that said Letters Patent is hereby corrected as shown below:

Col. 4, claim 1(c), line 49, delete "hyperdermic" and insert --hypodermic--.

Col. 5, claim 6, line 5, delete "hyperdermic" an insert --hypodermic--.

Col. 5, claim 10(c), line 23, delete "hyperdermic" and insert --hypodermic--.

Col. 6, claim 16(e), line 21, delete "hyperdermic" and insert --hypodermic--.

Signed and Sealed this

Twenty-first Day of September, 1999

Attest:

Q. TODD DICKINSON

*Attesting Officer*     *Acting Commissioner of Patents and Trademarks*